(12) United States Patent
Lee et al.

(10) Patent No.: US 10,564,433 B2
(45) Date of Patent: Feb. 18, 2020

(54) WEARABLE DEVICE

(71) Applicant: AMOGREENTECH CO., LTD., Gyeonggi-do (KR)

(72) Inventors: Gi Wook Lee, Gyeonggi-do (KR); Seung Yun Rho, Gyeonggi-do (KR); Dong Woo Kim, Chungcheongnam-do (KR); Seung Gon Park, Chungcheongnam-do (KR); Mun Su Yim, Gyeonggi-do (KR)

(73) Assignee: AMOGREENTECH CO., LTD., Gyeonggi-do (KR)

( * ) Notice: Subject to any disclaimer, the term of this patent is extended or adjusted under 35 U.S.C. 154(b) by 0 days.

(21) Appl. No.: 16/069,816

(22) PCT Filed: Jan. 12, 2017

(86) PCT No.: PCT/KR2017/000401
§ 371 (c)(1),
(2) Date: Jul. 12, 2018

(87) PCT Pub. No.: WO2017/123017
PCT Pub. Date: Jul. 20, 2017

(65) Prior Publication Data
US 2019/0033602 A1 Jan. 31, 2019

(30) Foreign Application Priority Data
Jan. 12, 2016 (KR) .................... 10-2016-0003762

(51) Int. Cl.
*G09G 5/00* (2006.01)
*G02B 27/01* (2006.01)
(Continued)

(52) U.S. Cl.
CPC ............ *G02B 27/0176* (2013.01); *A61F 9/02* (2013.01); *A61F 9/029* (2013.01); *A61F 9/04* (2013.01);
(Continued)

(58) Field of Classification Search
CPC .. G02B 27/01; G02B 27/0163; G02B 27/017; G02B 27/0176; G02B 2027/0178;
(Continued)

(56) References Cited

U.S. PATENT DOCUMENTS 6,369,952 B1    4/2002  Rallison et al.
10,090,556 B2 * 10/2018 Rho ........................ H01M 2/02
(Continued)

FOREIGN PATENT DOCUMENTS

JP         2012140709        7/2014
KR      1020090006896        1/2009
(Continued)

OTHER PUBLICATIONS

International Search Report and Written Opinion issued in International Patent Application No. PCT/KR2017/000401, dated May 10, 2017.
(Continued)

*Primary Examiner* — Joe H Cheng
(74) *Attorney, Agent, or Firm* — Norton Rose Fulbright US LLP

(57) ABSTRACT

A wearable device is provided. A wearable device according to an exemplary embodiment of the present invention comprises: a body unit comprising at least one function module; a wearing unit that has a predetermined length and is connected to the body unit such that the body unit remains worn on the user's face; and at least one flexible battery embedded in the wearing unit so as to provide the body unit with power such that the function module can be driven.

11 Claims, 8 Drawing Sheets

(51) Int. Cl.
*H01M 10/04* (2006.01)
*H01M 2/10* (2006.01)
*G06F 1/16* (2006.01)
*G01S 19/01* (2010.01)
*A61F 9/02* (2006.01)
*A61F 9/04* (2006.01)
*A63B 33/00* (2006.01)
*H01M 2/02* (2006.01)
*A63B 71/06* (2006.01)

(52) U.S. Cl.
CPC ............ *A63B 33/002* (2013.01); *G01S 19/01* (2013.01); *G06F 1/163* (2013.01); *G06F 1/1635* (2013.01); *G09G 5/003* (2013.01); *H01M 2/026* (2013.01); *H01M 2/0275* (2013.01); *H01M 2/10* (2013.01); *H01M 2/1066* (2013.01); *H01M 10/0436* (2013.01); *A63B 2071/0666* (2013.01); *G02B 2027/0152* (2013.01); *G02B 2027/0178* (2013.01); *G09G 2330/02* (2013.01); *H01M 2220/30* (2013.01)

(58) Field of Classification Search
CPC .......... G02B 2027/0187; H01M 2/026; H01M 2/0275; H01M 2/10; H01M 2/1022; G09G 5/003; G09G 2330/02
See application file for complete search history.

(56) References Cited

U.S. PATENT DOCUMENTS

| | | | | |
|---|---|---|---|---|
| 2013/0101884 A1* | 4/2013 | Ueda | ................... | H01M 10/052 429/127 |
| 2013/0188080 A1* | 7/2013 | Olsson | ..................... | G09G 5/00 348/333.01 |
| 2013/0235331 A1 | 9/2013 | Heinrich et al. | | |
| 2015/0016035 A1 | 1/2015 | Tussy | | |
| 2015/0253574 A1* | 9/2015 | Thurber | ............. | G02B 27/0172 359/630 |
| 2016/0011425 A1* | 1/2016 | Thurber | ................. | G02B 27/64 345/8 |
| 2016/0062125 A1* | 3/2016 | Baek | ................... | G02B 27/0176 361/679.01 |
| 2016/0300108 A1* | 10/2016 | Willis | ................... | G06K 9/0061 |
| 2016/0315647 A1* | 10/2016 | Moon | ................... | H04B 1/3822 |
| 2018/0132738 A1* | 5/2018 | Choi | ................... | H01M 2/1066 |
| 2018/0206023 A1* | 7/2018 | Lee | ...................... | H04R 1/1025 |

FOREIGN PATENT DOCUMENTS

| | | |
|---|---|---|
| KR | 1020120040454 | 4/2012 |
| KR | 1020150079440 | 7/2015 |
| KR | 1020150109229 | 10/2015 |
| KR | 1020150126268 | 11/2015 |
| KR | 1020160001229 | 1/2016 |

OTHER PUBLICATIONS

Office Action issued in corresponding Chinese Patent Application No. 201780006208, dated Sep. 17, 2019.

* cited by examiner

WEARABLE DEVICE

FIELD OF THE DISCLOSURE

The present invention relates to a wearable device, and more specifically, to a wearable device capable of implementing a reduction in weight and diversification of design even while increasing battery capacity.

DESCRIPTION OF RELATED ART

Recently, a display device having a shape mountable on a head of a user has been developed as a device configured to display visual information to the user in various forms according to development of an electronic technology.

That is, the display device mountable on the head of the user refers to a head mounted display device (HMD device). The above-described HMD device includes a virtual reality device configured to show a virtual reality world through a display panel close to eyes of the user, an augmented reality device configured to show both a real world and an augmented screen, and the like.

In the case of the above-described HMD device, a battery configured to drive various functions is required, and a prismatic type battery or a coin type battery is used.

Meanwhile, necessity for mounting a battery having a high condensing capacity has been increasing so that the user may use the HMD device for a long time. However, the size of a battery becomes larger when a condensing capacity becomes greater. Accordingly, since an additional space is necessary to mount the battery having the greater capacity in the HMD device, an overall size of the HMD device will increase, and since an increase of the space for mounting the battery causes a decrease of design freedom, the variety of design is hindered.

Further, in a case of the general prismatic type battery or coin type battery, since a weight remarkably increases when the condensing capacity increase, the weight of the HMD device increases.

SUMMARY OF THE INVENTION

The present invention is directed to providing a wearable device capable of implementing a reduction in weight and diversification of design even while increasing battery capacity.

The present invention provides a wearable device including a body unit which includes at least one function module; a wearing unit which has a predetermined length, is connected to the body unit, and is configured to maintain a state in which the body unit is worn on a face of a user; and at least one flexible battery embedded in the wearing unit to provide power to the body unit so that the function module is drivable.

The wearing unit may be detachably coupled to the body unit.

The body unit may include a control unit configured to control an overall operation of the function module, the wearing unit may include at least one contact terminal on an end portion thereof, and the flexible battery may be electrically connected to the control unit through the contact terminal when the body unit and the wearing unit are coupled.

The wearing unit may include a band member formed of a flexible material and connected to the body unit, and the flexible battery may be embedded in the band member. In this case, the band member may be formed of a soft material including at least one selected from leather, synthetic resin, a fabric, and silicon.

The wearing unit may be formed of the band member which has a predetermined length, and both end portions of the band member may be connected to the body unit.

The wearing unit may include a pair of band members connected to both end portions of the body unit, and a connection member configured to be variable in a length while connecting the pair of band members, and the flexible battery may be embedded in at least one side of the pair of band members.

The wearing unit may include a pair of frame members each having a predetermined length, being formed of a rigid material, and having one end portion connected to the body unit, and the flexible battery may be embedded in at least one side of the pair of frame members.

The function module may include at least one of a display unit including at least one of an augmented reality display and a virtual reality display, a fog prevention unit, a communication module, a GPS module, a sensor module, and a camera unit.

The wearable device may be implemented with an augmented reality device or a virtual reality device.

The body unit may be any one of a goggle type and a glasses type.

The flexible battery may include an electrode assembly; and a packing material in which the electrode assembly is encapsulated together with an electrolyte, wherein the electrode assembly and the packing material may be formed such that patterns for contraction and extension in a longitudinal direction are disposed to be coincident with each other when being bent.

The pattern may be provided such that a plurality of mountain parts and a plurality of valley parts are alternately formed in the longitudinal direction, and the mountain part and the valley part may be provided to have one section among an arc-shaped cross section, a polygonal cross section, and a section in which the above types of sections are combined.

The pattern may be entirely or partially formed on the electrode assembly and the packing material.

According to the present invention, since a film-shaped flexible battery of which a weight is relatively light per a condensing capacity is mounted and used as a driving power source, a weight of the device can be remarkably reduced in comparison with a conventional wearable device in which a prismatic type battery is embedded.

Further, according to the present invention, since the flexible battery is installed at a wearing unit rather than a body unit in which a function module is embedded, the body unit can have a minimized size or be easily implemented with various shapes. That is, a wearable device according to the present invention can maintain a worn state without slipping down or coming off when the body unit is implemented with a head mount type or even into a glasses type.

In addition, since the wearing unit in which the flexible battery is embedded can be detachably coupled to the body unit, and thus conveniently changed when power of the battery has completely run out, the present invention can have improved convenience of use.

DETAILED DESCRIPTION OF THE INVENTION

Figure 1:
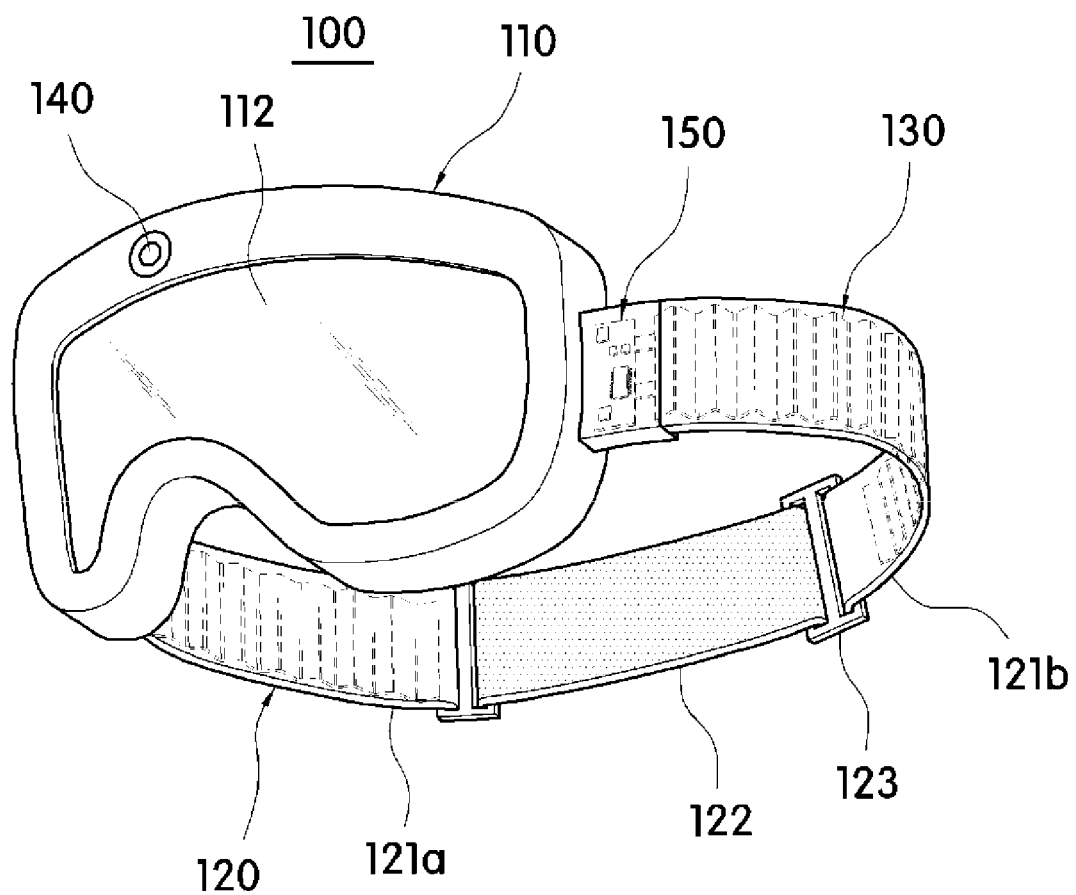
FIG. 1 is a view illustrating a wearable device according to an embodiment of the present invention.

Hereinafter, exemplary embodiments of the present invention will be described in detail with reference to the accompanying drawings which may allow one of ordinary skill in the art to easily perform the present invention. The present invention may be implemented in various forms and is not limited to the following embodiments. Components not related to the description are omitted in the drawings to clearly describe the present invention, and the same reference symbols are used for the same or similar components in the description.

Wearable devices 100, 200, and 300 according to an embodiment of the present invention are provided to allow a user to check various information or images displayed through a display unit while in a state of being worn on a head of a user as a head mounted display (HMD) device configured to implement visual virtual reality or augmented reality, and as shown in FIGS. 1 to 5, includes body units 110, 210, and 310, wearing units 120, 220, and 320, and a flexible battery 130.

That is, since the wearable devices 100, 200, and 300 according to the present invention may fix the body units 110, 210, and 310 on the head of the user through the wearing units 120, 220, and 320, the user may check various kinds of image information displayed through the display unit included in the body units 110, 210, and 310.

To this end, the body units 110, 210, and 310 may include various function modules configured to perform predetermined functions, such as the display unit, and may also include a control unit configured to control overall operations of the various function modules. Here, the control unit may be a microprocessor, and the display unit may be an augmented reality display or a virtual reality display.

Figure 4:
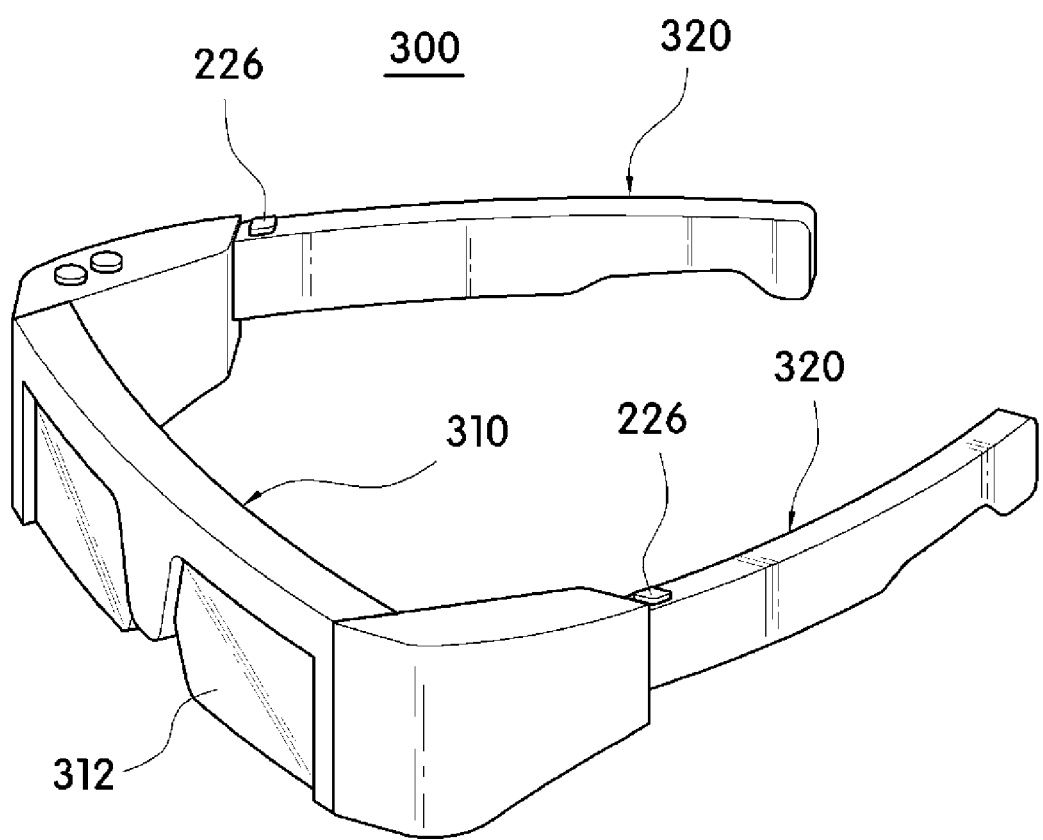
FIG. 4 is a view illustrating a wearable device according to still another embodiment of the present invention.
Figure 5:
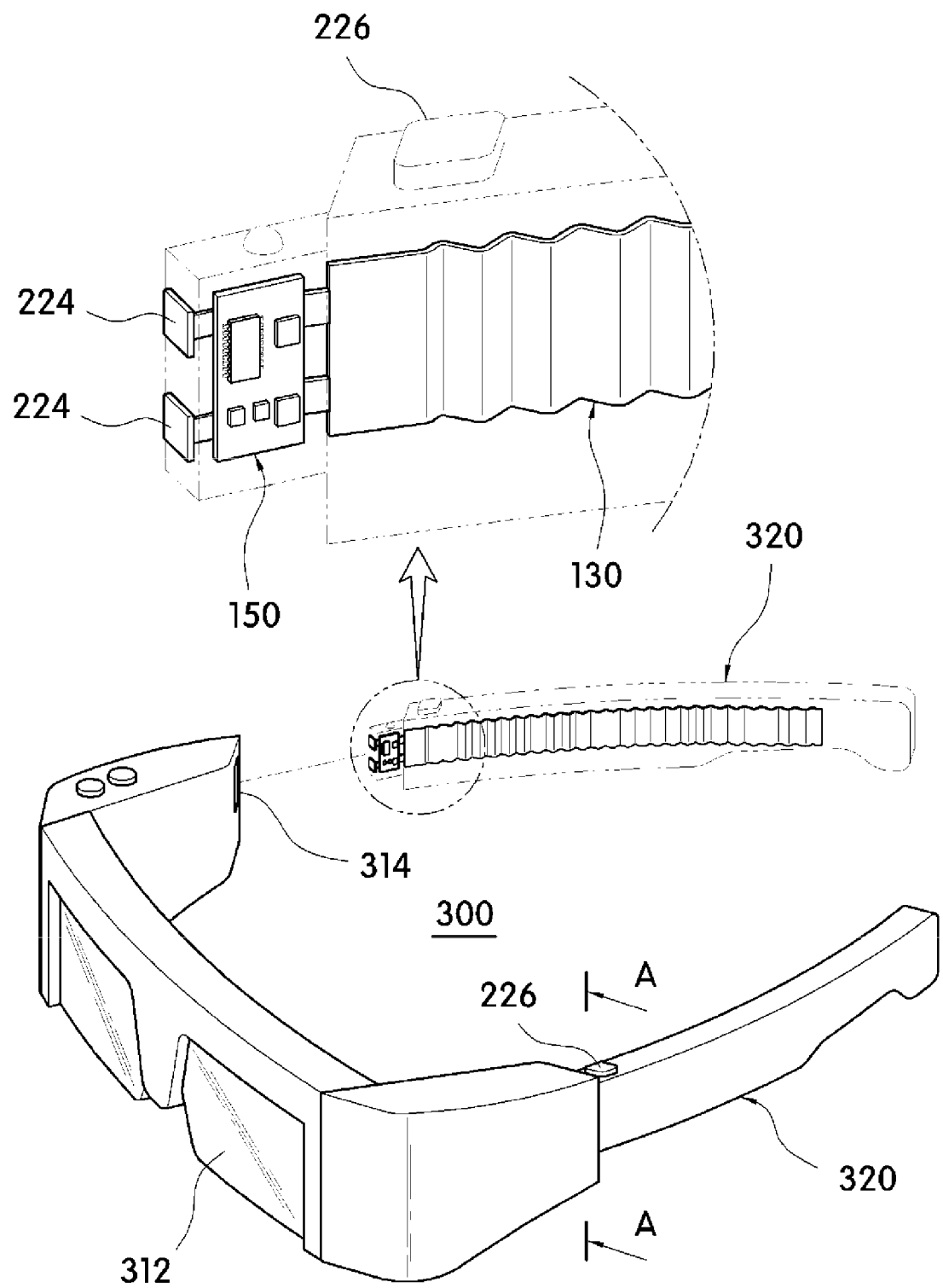
FIG. 5 is a view illustrating a state in which a wearing unit is separated apart from a body unit in FIG. 4.

As an example, as shown in FIGS. 1, 4, and 5, the body units 110 and 310 may each be an augmented reality device configured to show a real image and a virtual image which overlap each other as one image by each including the augmented reality display and transmission parts 112 and 312 formed of a transmissible material and being disposed at a location corresponding to both eyes of the user when worn so that the user may watch the front thereof.

As a specific example, the augmented reality device may be a smart snow goggle configured to show various information such as a velocity, a running time, a rear image, a front image, and the like on the augmented reality display or on the transmission parts 112 and 312 disposed in front of eyes of a wearer through a HUD (head-up display) function, or it may be a smart swimming goggle configured to show various information such as a running distance of a wearer, running time, a water temperature, etc.

Further, the augmented reality display may be a transparent organic light emitting display, and the transparent organic light emitting display may have a shape disposed on one surface of each of the transmission parts 112 and 312. Accordingly, the user may experience the augmented reality in which a real world which is seen by the eyes through the transmission parts 112 and 312, and information or an image output on the transparent organic light emitting display overlap each other.

However, the augmented reality device is not limited thereto and all of disclosed various augmented reality devices may be applied. Further, the information displayed on the augmented reality display may be disclosed to include various information suitable for an intended use other than the above-described information.

Figure 2:
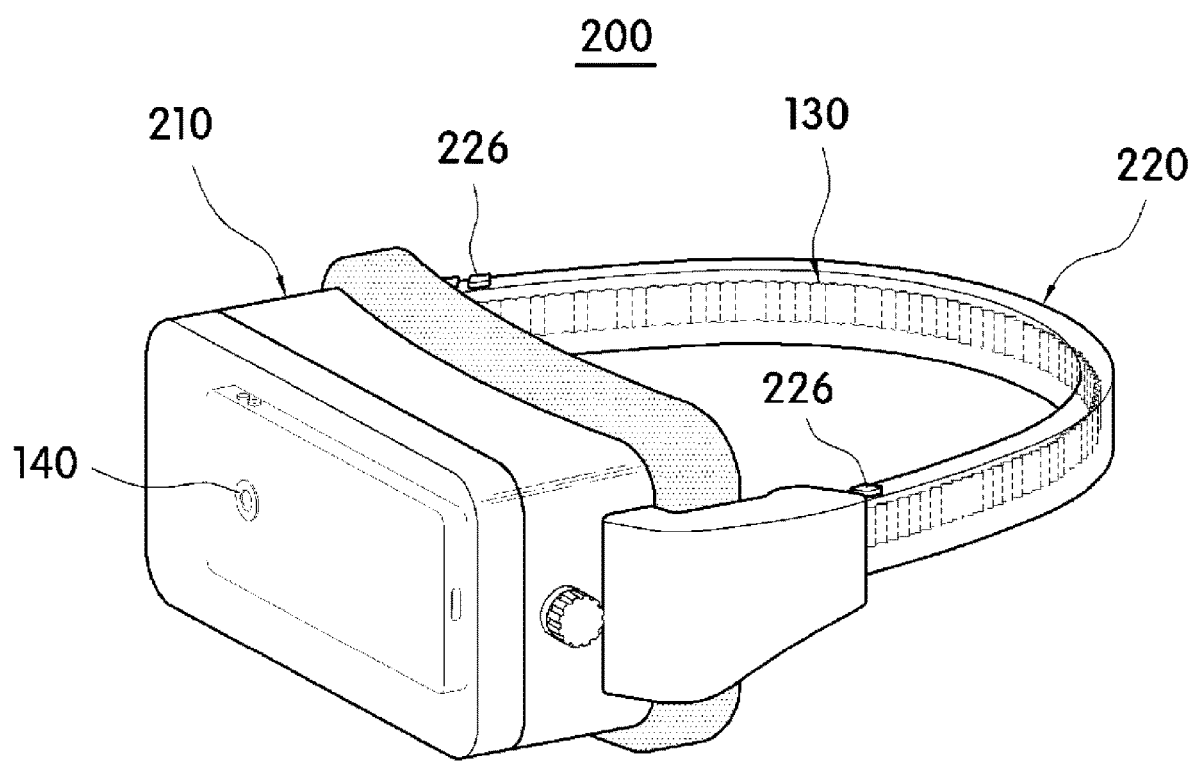
FIG. 2 is a view illustrating a wearable device according to another embodiment of the present invention.
Figure 3:
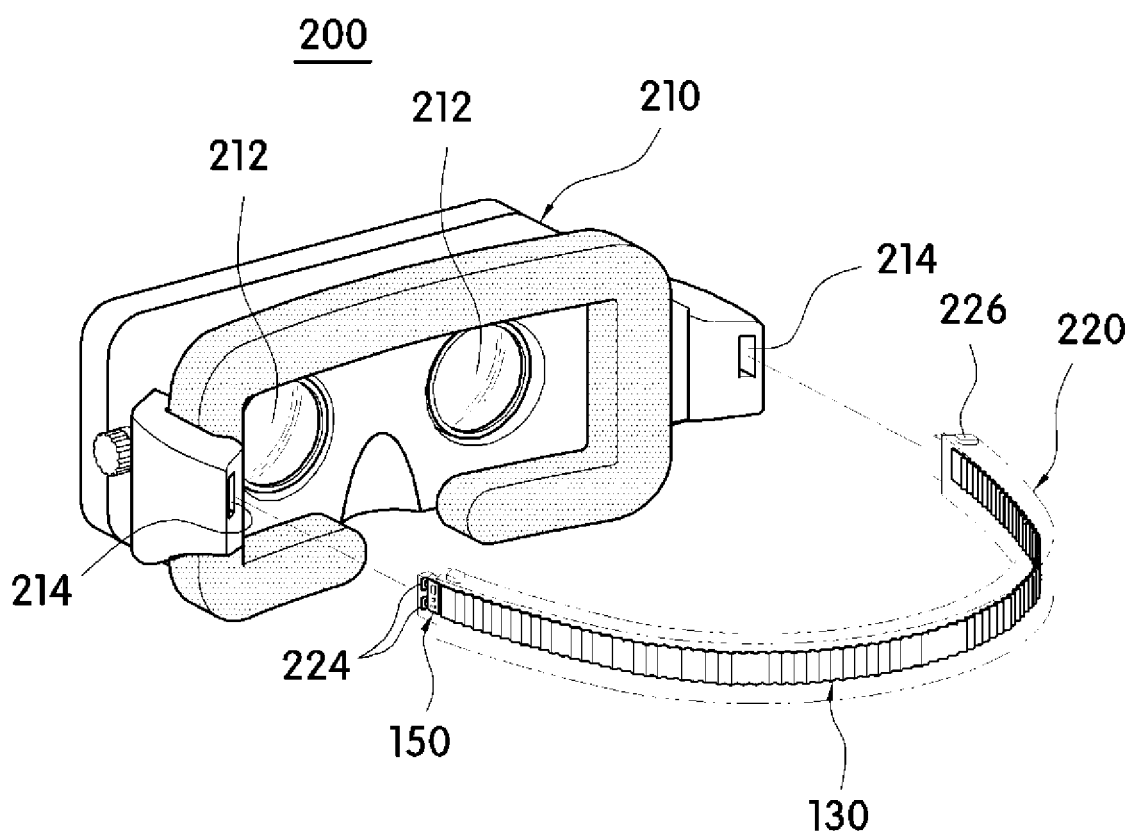
FIG. 3 is a view illustrating a state in which a wearing unit is separated apart from a body unit in FIG. 2.

Further, as shown in FIGS. 2 and 3, the body unit 210 may be a virtual reality device including an optical lens 212 and the virtual reality display to make a wearer appear to interact with surroundings or an environment in reality by copying a particular environment or situation as it is in reality.

As a specific example, the virtual reality device may be a simulator for simulation training such as pilot training, or a simulator for medical simulation such as virtual surgery procedure, but may be not limited thereto and all of disclosed various virtual reality devices may be applied.

As shown in FIGS. 1 to 3, the above-described body units 110 and 210 may be a goggle type fixed to a head of the user through the wearing units 120 and 220 each having a band shape with one side configured to come into contact with a face of the user and formed of a flexible material.

Further, as shown in FIGS. 4 and 5, the body unit 310 may be a glasses type in which the wearing unit 320 having a shape of a pair of frame members formed of a rigid material such as plastic or metal is hooked on ears of the user.

Meanwhile, the body units 110, 210, and 310 according to the present invention may include other function modules to perform various functions other than the display unit. As an example, the body units 110, 210, and 310 may include at least one among a fog prevention unit configured to prevent fog in a transmission window or the display unit, a communication module configured to transmit and receive data in a wireless method, a GPS module configured to track a location of the user, various sensor modules configured to sense a gesture, movement, a temperature, a velocity, and the like of the wearer, a camera unit configured to gain surrounding image information of the wearer, a mike unit, and a speaker unit. In addition, the body units 110, 210, and 310 may further include a data storage unit configured to store the information obtained through the above-described function module, and the like and may further include a data terminal capable of inputting and outputting the data to and from an external device through a wired method.

Accordingly, the user may store image data recorded by the camera unit 140 in the data storage unit while the user is in a state of wearing the wearable devices 100, 200, and 300 according to the present invention, and then transmit the stored image data to an external device such as a computer or a smart phone through the communication module to play the recorded image data.

The wearing units 120, 220, and 320 are provided so that the user may wear the wearable devices 100, 200, and 300 according to the present invention, and the body units 110, 210, and 310 maintain a state of being located on the face of the user.

To this end, the wearing units 120, 220, and 320 may each have a predetermined length and at least one side connected to the body units 110, 210, and 310.

In this case, each of the wearing units 120, 220, and 320 may have a band shape formed of the flexible material as described above, and may be a pair of frame members formed of a material having rigidity.

As an example, as shown in FIG. 1, the wearing unit 120 may have a band shape including a pair of band members 121*a* and 121*b* connected to both sides of the body unit 110, respectively, and a connection member 122 configured to connect the pair of band members 121*a* and 121*b*, and thus may have a shape which surrounds the head of the user.

In this case, the pair of band members 121*a* and 121*b* and the connection member 122 may be formed of a flexible soft material, and since a length of the connection member 122 is variable, an interval between the pair of band members 121*a* and 121*b* may be adjustable. As an example, the pair of band members 121*a* and 121*b* may be formed of a material including at least one selected from leather, synthetic resin, and silicon.

Accordingly, since the entire length of the wearing unit 120 is variable through the connection member 122, the wearable devices 100, 200, and 300 according to the embodiment of the present invention may be conveniently worn even when users have various head sizes.

Here, the connection member 122 may have a shape of which the entire length is adjusted because an engaging member 123, in which a plurality of slits are formed, is disposed at a center of the length to adjust a location at which the connection member 122 passes through the slits. Alternatively, the connection member 122 may be formed of a flexible and elastic material. Accordingly, the connection member 122 may have the entire length which is elongated by an applied external force and returns to an original length when the external force is removed in a wearing process. However, a method of adjusting the entire length of each of the wearing units 120, 220, and 320 is not limited thereto, and all of disclosed methods may be applied as a method of adjusting the length when the two members are connected.

As another example, as shown in FIGS. 2 and 3, the wearing unit 220 may be formed of a flexible material having a predetermined length, and may have a band shape of which both end portions are connected to the body unit 210. In this case, the wearing unit 220 may have both the flexibility and elasticity, and thus may have a shape of which the entire length is elongated by an external force and returns to the original length when the external force is removed.

As still another example, as shown in FIGS. 4 and 5, the wearing unit 320 may be a pair of frame members each having a predetermined length, formed of a rigid material, and connected to the body unit 310. Accordingly, the user may wear the wearable device 300 according to the embodiment in a wearing method the same as that of glasses.

The flexible battery 130 is provided to serve as a power supply source configured to supply driving power to the body units 110, 210, and 310. That is, since the flexible battery 130 provides the driving power to a control unit (not shown) embedded in the body units 110, 210, and 310, the above-described function module included in each of the body units 110, 210, and 310 may be driven by control of the control unit.

In this case, the flexible battery 130 applied to the present invention may have a plate shape having a predetermined area and length, and flexibility, and at least one flexible battery 130 may be embedded in each of the wearing units 120, 220, and 320.

That is, in each of the wearable devices 100, 200, and 300 according to the present invention, the flexible battery 130 configured to serve as the power supply source is not embedded in each of the body units 110, 210, and 310, but rather in each of the wearing units 120, 220, and 320 configured to maintain a worn state of each of the body units 110, 210, and 310. Accordingly, unlike a conventional wearable device in which a battery is installed in a body unit including a function module, since each of the body units 110, 210, and 310 does not require a space for mounting the battery, minimization of size and thinning may be implemented by decreasing a whole size of each of the body units 110, 210, and 310.

Further, since the mounting space of the battery is omitted in each of the body units 110, 210, and 310, an additional function module other than the above described function module may be further included by improving space usability of each of the body units 110, 210, and 310 even while maintaining the size of each of the body units, and thus more various functions may be implemented, and change into various designs may be simple.

In addition, since each of the body units 110, 210, and 310 applied to the wearable devices 100, 200, and 300 according to the present invention may have a reduced weight equivalent to a weight of the battery unlike the conventional wearable device, the user may be prevented from leaning in a forward direction due to the heavy body units 110, 210, and 310 in a wearing state, and thus wearability may be improved.

In addition, each of the wearable devices 100, 200, and 300 according to the present invention may use the flexible battery having a relatively lighter weight per a condensing capacity rather than a prismatic type battery having a relatively greater weight per a condensing capacity to reduce a whole weight of the device and then implement a reduction in weight. As an example, since a weight of a prismatic type battery having a condensing capacity of 4000 mAh is approximately 1 kg, but a weight of a flexible battery 130 having a condensing capacity of 4000 mAh is approximately 120 g, the flexible battery may have a condensing capacity equivalent to that of the prismatic type battery even when having a weight approximately one tenth of that of the prismatic type battery.

That is, each of the wearable devices 100, 200, and 300 according to the present invention may use the flexible battery 130 having a relatively lighter weight per a condensing capacity to remarkably reduce the weight thereof in comparison with the conventional wearable device in which the prismatic type battery is embedded. Accordingly, since the wearable devices 100, 200, and 300 according to the present invention may be reduced in a weight and have improved wearability when being worn by the user, activity may be improved. Further, since the wearable devices 100, 200, and 300 according to the present invention may be reduced in the weight through usage of the flexible battery 130, and the wearable devices 100, 200, and 300 according to the present invention may each have remarkably decreased probability of a worn state being released even when implemented with not only the goggle type of which the worn state is maintained through the band shape wearing units 120 and 220, but also the glasses type of which the worn state is maintained through the pair of frame members type wearing unit 320.

Specifically, the flexible battery 130 may be embedded in at least one of the pair of band members 121*a* and 121*b* in a case in which the wearing unit 120 includes the pair of band members 121*a* and 121*b* formed of a soft material and the connection member 122 as shown in FIG. 1, and the flexible battery 130 may have a length approximately the same as that of one body to be embedded in the one body in a case in which the wearing unit 220 is formed of the one body formed of a soft material and has both end portions connected to both ends of the body unit 210 as shown in FIGS. 2 and 3.

Further, as shown in FIGS. 4 and 5, in a case in which the wearing unit 320 is formed of the pair of frame members, the flexible battery 130 may be embedded in at least one of the pair of frame members.

As described above, in the wearable devices 100, 200, and 300 according to the present invention, the flexible battery which is the power supply source may be embedded in each of the wearing units 120, 220, and 320, and thus the body units 110, 210, and 310 may be reduced in the weight, and since the number of used flexible batteries 130 is increased or a flexible battery 130 having a relatively greater length is used to increase the condensing capacity of the battery, the weight of each of the body units 110, 210, and 310 is prevented from increasing even when a whole weight of each of the wearing units 120, 220, and 320 in which the battery is embedded increases, and thus an unrestrained condensing capacity may be implemented while minimizing reduction of wearability.

Meanwhile, in the wearable devices 200 and 300 according to the present invention, the wearing units 220 and 320 each having the flexible battery 130 embedded therein may be detachably coupled to the body units 210 and 310. Accordingly, when power of the flexible battery 130 embedded in each of the wearing units 220 and 320 is partially or completely consumed or performance of the flexible battery 130 is lowered due to repetitive use to be replaced with another battery, the wearing units 220 and 320 may be separated from the body units 210 and 310 to be conveniently replaced with other wearing units.

Further, the wearing units 220 and 320 separated from the body units 210 and 310 after partial or complete consumption of the power of the flexible battery 130 may be reused by recharging the flexible battery 130 through an external charging device.

To this end, each of the wearing units 220 and 320 may include contact terminals 224, which are outwardly exposed, on end portions thereof, and accommodation grooves 214 and 314, into which the end portions of the wearing units 220 and 320 are inserted, may each be formed in the body units 210 and 310. Further, since each of the accommodation grooves 214 and 314 include terminals to be contacted (not shown) corresponding to the contact terminals 224, when the end portions of the wearing units 220 and 320 are each inserted into the accommodation grooves 214 and 314, the contact terminals 224 and the terminals to be contacted may come into contact with each other.

Here, the contact terminals 224 and the terminals to be contacted may be a type provided in pairs and divided into a positive electrode and a negative electrode. The contact terminals 224 and the terminals to be contacted may also be a micro-pin or USB port type in which a positive electrode and a negative electrode are combined. Further, since a circuit part 150 is embedded in each of the wearing units 220 and 320 with the flexible battery 130, charging and discharging of the flexible battery 130 may be controlled, and the circuit part 150 may include a protection circuit to prevent overcharge of the flexible battery 130.

Accordingly, the control unit embedded in each of the body units 210 and 310 may be electrically connected to the flexible battery 130 to receive power from the flexible battery 130 when the body units 210 and 310 are coupled to the wearing units 220 and 320.

Further, exhausted power in each of the wearing units 220 and 320 separated from the body units 210 and 310 may be charged using power provided from an external charging device.

In this case, as shown in FIGS. 2 to 5, the wearing units 220 and 320 may include a restraint part configured to restrain or release a state in which the wearing units 220 and 320 are coupled to the body units 210 and 310. Accordingly, when the user does not operate the restraint part, the wearable devices 200 and 300 according to the present invention may prevent separation of the wearing units 220 and 320 from the body units 210 and 310 which occurs regardless of an intention of the user.

As an example, the restraint part may include a button 226, which may be pressed by the user to be operated, in one side of each of the wearing units 220 and 320, and a button method, in which a restrained state of each of the wearing units 220 and 320 inserted into each of the accommodation grooves 214 and 314 may be released when the user presses the button 226, and the wearing units 220 and 320 may return to an original state when a pressing force to the button 226 is removed, may be applied. However, the restraint part is not limited thereto, and all of various known methods such as a pin insertion method, a clip method, a pressing method, a thread coupling method, and the like may be applied.

Meanwhile, as shown in FIG. 1, in a case in which the wearing unit 120 is coupled to the body unit 110 to prevent separation, the circuit part 150 configured to control charge and discharge of the flexible battery 130 may be embedded in the wearing unit 120, and a charging port (not shown) connected to the circuit part 150 may be formed at one side of the wearing unit 120, and thus the flexible battery 130 may be recharged through the charging port.

Further, although not shown in the drawings, the wearing unit 120 applied in FIG. 1 is also detachably coupled to the body unit 110 in a method equivalent to the above described method, and thus the wearing unit 120 may be conveniently separated from the body unit 110 to be replaced when necessary to be replaced.

In addition, the wearable devices 100, 200, and 300 according to the present invention may be configured to include a type in which the three types of the wearing units 120, 220, and 320 and the body units 110, 210, and 310 shown in FIGS. 1 to 5 are each combined.

Figure 6:
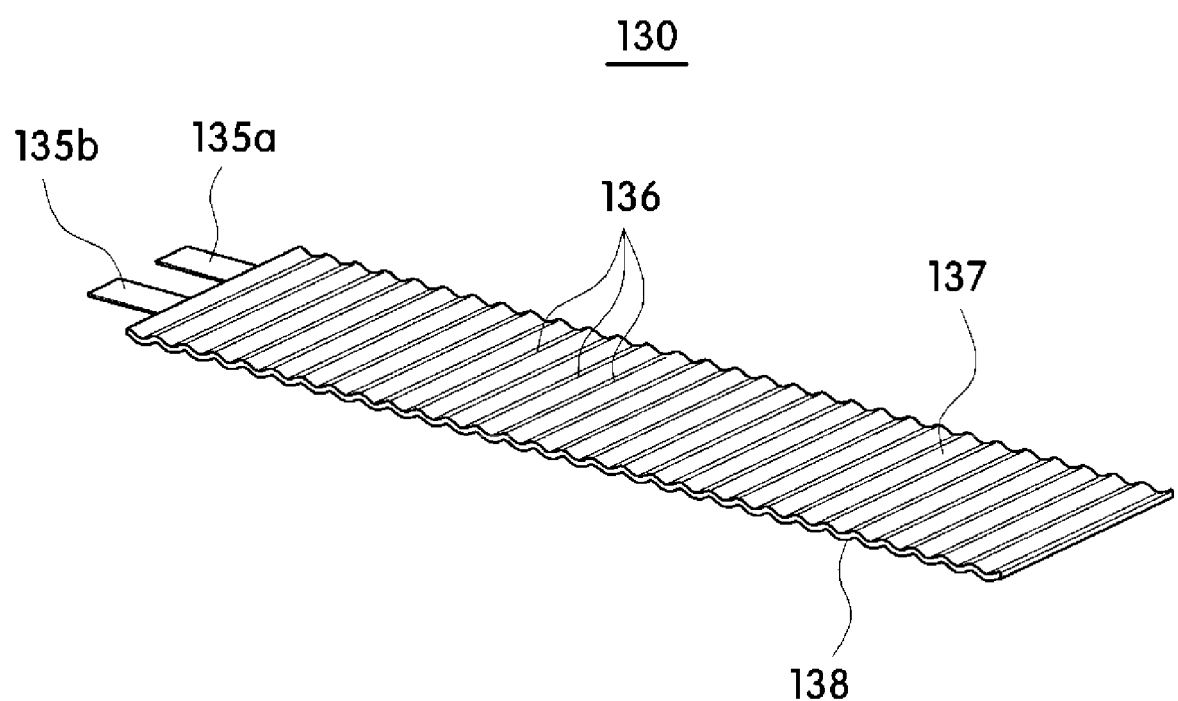
FIG. 6 is a schematic view illustrating a flexible battery applicable to the wearable device according to the present invention.
Figure 7:
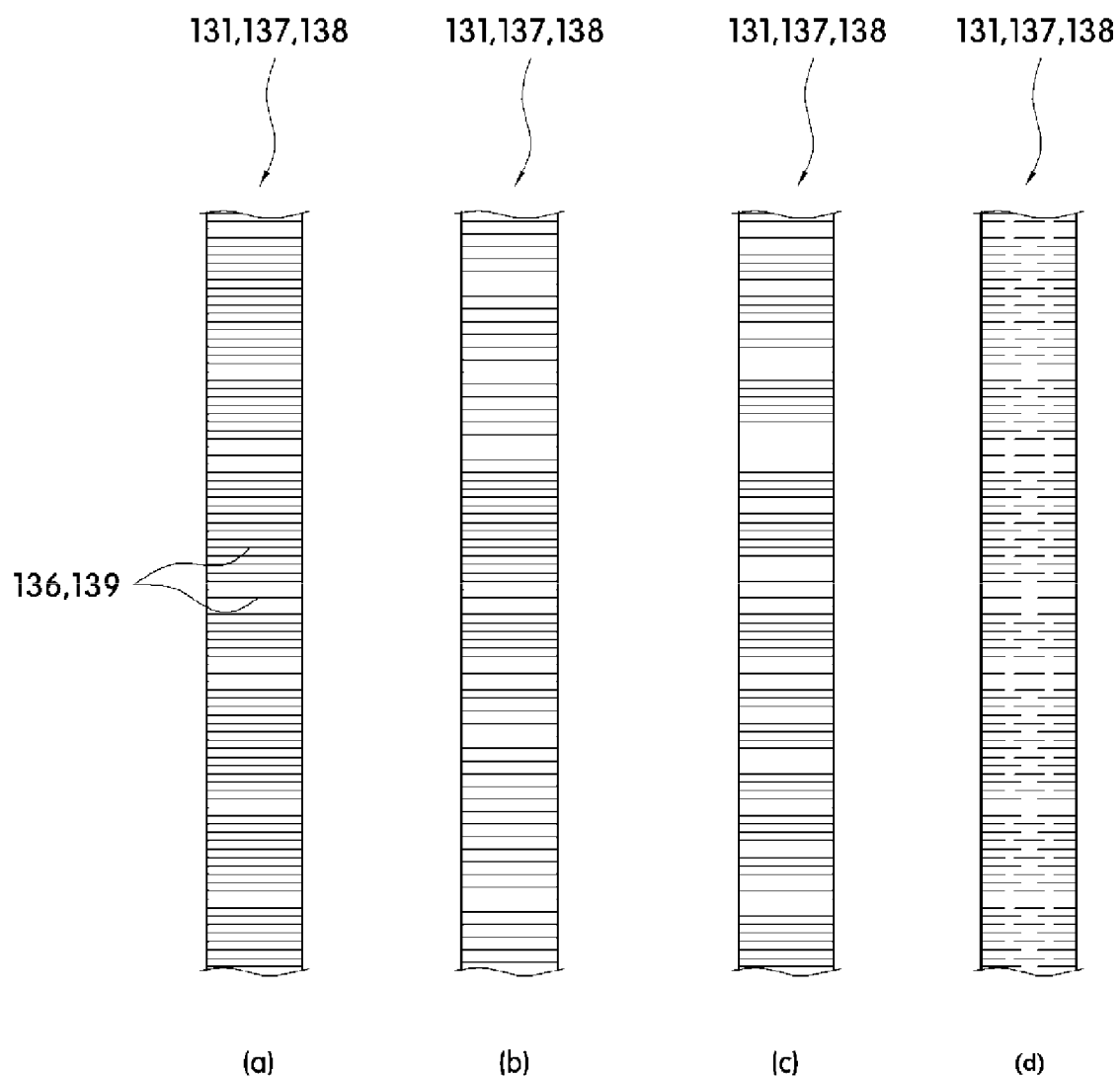
FIG. 7 is a view illustrating various intervals of valley parts or mountain parts adjacent to each other, as an exemplary view illustrating various patterns applied to an electrode assembly and a packing material in FIG. 6.
Figure 8:
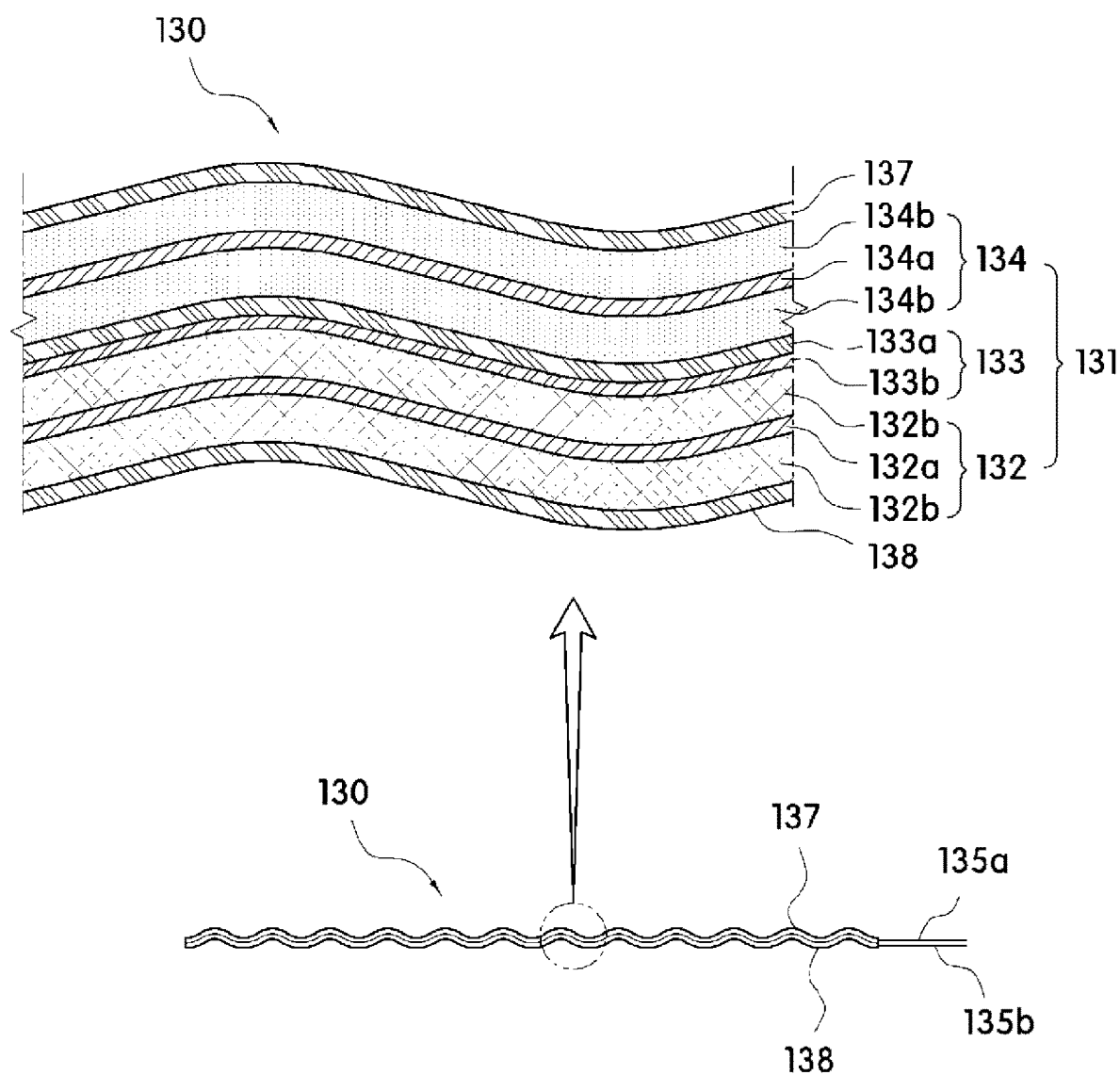
FIG. 8 is an enlarged cross-sectional view illustrating a detailed configuration in FIG. 6.

Meanwhile, as shown in FIGS. 6 to 8, the flexible battery 130 applied to the present invention may be a type in which the electrode assembly 131 is encapsulated together with an electrolyte in packing materials 137 and 138.

In this case, the flexible battery 130 applied to the present invention may include patterns 136 and 139, which are for contraction and relaxation in a longitudinal direction, in the electrode assembly 131 as well as in the packing materials 137 and 138. Both the first pattern 139 formed in the packing materials 137 and 138 and the second pattern 136 formed in the electrode assembly 131 may be provided to have the same directionality.

Accordingly, as shown in FIGS. 1 to 3, a deformation amount of a base material itself forming the electrode assembly 131 and the packing materials 137 and 138 may be prevented or minimized through the patterns 136 and 139 even though the flexible battery 130 is embedded in each of the flexibly-band-type wearing units 120, 220, and 320, and the flexible battery 130 is bent or distorted with the wearing units 120, 220, and 320 during a using process. Accordingly, since the deformation amount of the base material itself which may occur in a bending portion is minimized even though the flexible battery 130 is bent, the electrode assembly 131 and the packing materials 137 and 138 may be prevented from damage or performance degradation which occurs due to bending.

In this case, the first pattern 139 and the second pattern 136 may be disposed so that the first pattern 139 and the second pattern 136 not only have the same directionality but also are coincident with each other. The reason is to allow the first pattern 139 and the second pattern 136 to always behave equally.

As described above, since the patterns 136 and 139 for the contraction and relaxation in the longitudinal direction are each formed in the electrode assembly 131 as well as in the packing materials 137 and 138 to be coincident with each other in the flexible battery 130 applied to the present invention, the electrode assembly 131 and the packing materials 137 and 138 may always maintain a uniform interval or contact state for the entire length even though bending in the longitudinal direction. Accordingly, since the electrolyte encapsulated together with the electrode assembly 131 is uniformly distributed for the entire length of the flexible battery 130, battery performance degradation may be prevented in the flexible battery 130.

As an example, mountain parts and valley parts of each of the first pattern 139 and the second pattern 136 may be formed in a direction parallel to a width direction of each of the packing materials 137 and 138 as well as the electrode assembly 131, and the mountain parts and the valley parts may be alternately disposed along a longitudinal direction of each of the packing materials 137 and 138 and the electrode assembly 131. Further, regarding the mountain parts and the valley parts which constitute the first pattern 139 and the second pattern 136, the mountain parts are formed at the same positions, and the valley parts are formed at the same positions, such that the first pattern 139 and the second pattern 136 are matched with each other.

Specifically, the mountain parts and the valley parts of the first pattern 139 and second pattern 136 may be formed in a direction parallel to a straight line parallel to the width direction of each of the packing materials 137 and 138 and the electrode assembly 131 and may be formed to be repetitively disposed along the longitudinal direction.

In this case, each of the patterns 136 and 139 may be continuously or discontinuously formed in a direction parallel to the width direction of each of the packing materials 137 and 138 and the electrode assembly 131, may be formed for the entire length of each of the electrode assembly 131 and the packing materials 137 and 138, and may be partially formed for a partial length.

Here, each of the mountain parts and the valley parts may be provided to have one type of section among an arc-shaped section including a half circle, a polygonal section including a triangle or quadrangle, and a section in which the arc-shaped section and the polygonal section are combined, and each of the mountain parts and the valley parts may have the same pitch and width but may also have different pitches and widths from each other.

Accordingly, the packing materials 137 and 138 and the electrode assembly 131 may reduce fatigue applied to the base material itself through the patterns 136 and 139 even though embedded in the wearing units 120, 220, and 320 in a bent state, and thus it is possible to prevent damage or performance degradation as a battery.

Meanwhile, in the first pattern 139 and the second pattern 136, each of an interval of the mountain parts adjacent to each other or the valley parts adjacent to each other may be formed in the same interval or in different intervals, and may also be provided in a shape in which the same interval and the different intervals are combined.

Further, the first pattern 139 formed in the packing materials 137 and 138 may be formed in a whole surface of each of the packing materials 137 and 138 but may also be partially formed.

The electrode assembly 131 is provided to be encapsulated with the electrolyte in the packing materials 137 and 138, and includes a positive electrode 132, a negative electrode 134, and a separator 133.

The positive electrode 132 may include a positive electrode current collector 132a and a positive electrode active material 132b, while the negative electrode 134 may include a negative electrode current collector 134a and a negative electrode active material 134b, and each of the positive electrode current collector 132a and the negative electrode current collector 134a may be implemented with a plate shaped sheet type having a predetermined area.

That is, the positive electrode 132 and the negative electrode 134 may each have the active materials 132b and 134b compressed, deposited, or applied at one surface or both surfaces of the current collectors 132a and 134a. In this case, the active materials 132b and 134b may each be provided to correspond to whole areas of the current collectors 132a and 134a, and may also partially correspond to some of the areas.

Further, the positive electrode current collector 132a and the negative electrode current collector 134a may be formed with a negative electrode terminal 135a and a positive electrode terminal 135b, respectively, so as to be electrically connected to an external device. Here, the positive electrode terminal 135b and the negative electrode terminal 135a may each extend from the positive electrode current collector 132a and the negative electrode current collector 134a to be provided in a shape which protrudes from one sides of the packing materials 137 and 138, and to be provided to be exposed on surfaces of the packing materials 137 and 138.

In this case, each of the positive electrode active material 132b and the negative electrode active material 134b may include polytetrafluoroethylene (PTFE) ingredients. Accordingly, the positive electrode active material 132b and the negative electrode active material 134b may be prevented from peeling away from the current collectors 132a and 134a or cracking due to bending even when the flexible battery 130 is bent.

Meanwhile, the separator 133 disposed between the positive electrode 132 and the negative electrode 134 may include a nano fiber web layer 133b formed on one surface or both surfaces of a non-woven fabric layer 133a.

Here, the nano fiber web layer 133b may be a nano fiber including at least one selected from a polyacrylonitrile nano fiber and a polyvinylidene fluoride nano fiber.

The nano fiber web layer 133b may include only the polyacrylonitrile nano fiber to secure radioactivity and formation of uniform pores.

The packing materials 137 and 138 may be formed as a plate shaped member having a predetermined area and may protect the electrode assembly 131 from an external force by accommodating the electrode assembly 131 and the electrolyte therein.

As an example, the packing materials 137 and 138 may include a first packing material 137 and a second packing material 138 which are provided in a pair, and since edges of the packing materials 137 and 138 which come into contact with each other are sealed by an adhesive, exposure of the electrolyte and the electrode assembly 131 accommodated in the packing materials 137 and 138 to the outside may be prevented and the electrolyte may be prevented from leaking to the outside.

In the packing materials 137 and 138, the first packing material 137 and the second packing material 138 may be formed of two members and the edges forming a sealing part may be sealed by the adhesive. Alternatively, the packing materials 137 and 138 may be formed as one member, and the remaining portions which come into contact with each other may be sealed by the adhesive after being folded in half along a width direction or a longitudinal direction thereof.

Meanwhile, each of the wearable devices 100, 200, and 300 according to the present invention may be formed into a type which serves both an augmented reality function and a virtual reality function, may be a type in which the augmented reality function and the virtual reality function are combined, and may have the display unit on which information linked with a smart phone is displayed. Further, each of the wearable devices 100, 200, and 300 according to the present invention may be a type in which a smart phone having a virtual reality function is detachably coupled to each of the body units 110, 210, and 310 when being implemented with the virtual reality device. In this case, the display unit included in each of the body unit may be omitted, and the smart phone coupled to each of the body unit may substitute for the display unit.

Although one embodiment of the present invention is described above, the spirit of the present invention is not limited to the embodiment shown in the description, and although those skilled in the art may provide other embodiments due to addition, change, or removal of the components within the scope of the same spirit of the present invention, such embodiments and the above embodiments are also included in the scope of the spirit of the present invention.

The invention claimed is:

1. A wearable device comprising:
    a body unit including at least one function module;
    a wearing unit including a band member, which has a predetermined length, is formed of a flexible material, is connected to the body unit, and is configured to maintain a state in which the body unit is worn on a face of a user; and
    at least one flexible battery configured to provide power to the body unit so that the function module is drivable, wherein the flexible battery includes:
        an electrode assembly;
        a packing material in which the electrode assembly is encapsulated together with an electrolyte, and
        patterns respectively formed on the electrode assembly and the packing material to be coincident with each other for contraction and extension in a longitudinal direction when being bent,
    wherein the flexible battery is embedded in the band member such that the length direction of the flexible battery and the length direction of the band member are disposed in the same direction.

2. The wearable device of claim 1, wherein the wearing unit is detachably coupled to the body unit.

3. The wearable device of claim 1, wherein:
    the body unit includes a control unit configured to control an overall operation of the function module;
    the wearing unit includes at least one contact terminal on an end portion thereof; and
    the flexible battery is electrically connected to the control unit through the contact terminal when the body unit and the wearing unit are coupled.

4. The wearable device of claim 1, wherein the band member has a predetermined length and includes both end portions connected to the body unit.

5. The wearable device of claim 1, wherein:
    the wearing unit includes a pair of band members connected to both end portions of the body unit, respectively, and a connection member configured to be variable in a length while connecting the pair of band members; and
    the flexible battery is embedded in at least one side of the pair of band members.

6. The wearable device of claim 1, wherein the band member includes at least one material selected from leather, synthetic resin, a fabric, and silicon.

7. The wearable device of claim 1, wherein the function module further includes at least one of a display unit including at least one of an augmented reality display and a virtual reality display, a fog prevention unit, a communication module, a GPS module, a sensor module, and a camera unit.

8. The wearable device of claim 1, wherein the body unit includes an augmented reality device or a virtual reality device.

9. The wearable device of claim 1, wherein the body unit is a goggle type or a glasses type.

10. The wearable device of claim 1, wherein the pattern is provided such that a plurality of mountain parts and a plurality of valley parts are alternately formed in the longitudinal direction,
    wherein the mountain part and the valley part is provided to have one section among an arc-shaped cross section, a polygonal cross section, and a section in which the above types of sections are combined.

11. The wearable device of claim 1, wherein the patterns are entirely or partially formed on the electrode assembly and the packing material.

* * * * *